United States Patent [19]

Salazar

[11] Patent Number: 5,300,095
[45] Date of Patent: Apr. 5, 1994

[54] ELECTRO-MECHANICAL APPARATUS FOR TREATING PAIN

[76] Inventor: Angel Z. Salazar, 151-161 Avda. Hospital Militar, E-08034 Barcelona, Spain

[21] Appl. No.: 919,933

[22] Filed: Jul. 27, 1992

[30] Foreign Application Priority Data

Aug. 8, 1991 [ES] Spain .................. P 9101924

[51] Int. Cl.$^5$ ........................... A61N 1/02
[52] U.S. Cl. .................. 601/21; 607/150; 607/46; 607/154; 601/108
[58] Field of Search .............. 128/422, 421, 419 R, 128/24.2, 32, 36, 41, 54, 55, 24.5; 607/46, 48, 150

[56] References Cited

U.S. PATENT DOCUMENTS

| | | | |
|---|---|---|---|
| 1,680,086 | 8/1928 | Carlson | 128/41 |
| 2,021,968 | 11/1935 | Scheidegger | 128/41 |
| 4,187,837 | 2/1980 | Braun | 128/32 |
| 4,549,535 | 10/1985 | Wing | 128/55 |
| 4,566,442 | 1/1986 | Mabuchi et al. | 128/55 |
| 4,827,914 | 5/1989 | Kamazawa | 128/36 |
| 4,944,302 | 7/1990 | Hernandez et al. | |
| 5,140,979 | 5/1992 | Nakagawa | 128/421 |

FOREIGN PATENT DOCUMENTS

| | | | |
|---|---|---|---|
| 0330797 | 9/1989 | European Pat. Off. | 128/421 |
| 545122 | 2/1932 | Fed. Rep. of Germany | |
| 753157 | 10/1933 | France | |
| 2368285 | 5/1978 | France | |
| 549883 | 12/1985 | Spain | |
| 8801928 | 6/1988 | Spain | |
| 1513605 | 6/1978 | United Kingdom | |
| 1548917 | 7/1979 | United Kingdom | |

*Primary Examiner*—Lee S. Cohen
*Assistant Examiner*—Jeffrey R. Jastrzab
*Attorney, Agent, or Firm*—Steinberg & Raskin

[57] ABSTRACT

The present invention comprises a metal electrode (2) electrically insulated on the active surface thereof and which is connected to a high frequency circuit (4) and transmits current capacitatively. This apparatus is characterized in that an axial reciprocating movement of adjustable rate is applied to the electrode (2) and the intensity of the percussion on the patient's affected area is also adjustable. The electrode is removeably attached to a stem (7) resiliently engaging (21) the periphery of a cam (11) driven by a geared motor (13, 14) housed in a grip (16) of the mechanical device (1). This comprises a nozzle (17) through which the electrode (2) projects and which is provided with a replaceable front portion (18) for coupling portions of different length. The mechanical device (1) is connected to a box (3) containing the electronic circuit and the percussion rate control device for the electrode holder stem (7).

10 Claims, 1 Drawing Sheet

ELECTRO-MECHANICAL APPARATUS FOR TREATING PAIN

The present invention relates to a therapeutical apparatus.

The main purpose of this apparatus is to treat pain in general and pain caused by rheumatic affections in particular.

Treatment of pain has been the object of various studies and different methods and devices have been devised.

One of these apparatus is disclosed in Spanish patent of invention ES 549 883 and consists essentially of a metal electrode electrically insulated on the active surface thereof and connected to a high frequency circuit to transmit current capacitatively (hyperthermia). The area of the patient to be treated is massaged with this electrode, with a hydrating cream used therebetween. The apparatus further comprises a neutral electrode, also applicable to the patient.

Another method used for treating rheumatic pains is taught in Spanish patent of invention ES 8801928, consisting essentially of applying a combination of percussion and heat to the patient's affected area.

Although these known apparatus and methods alleviate the pain, and rarely cure the disease, certain problems are experienced with their application. These problems are overcome with the apparatus of the present patent at the same time as greater effectiveness from the point of view of curing the disease is achieved.

A concentration of focal power in the root and nerve canal routes is not achieved in capacitative electric transfer treatment where chronic osteoarticular inflammatory processes, causing the pain syndromes by osteophytosis, are present.

In the electro-mechanical percussion and heat treatment apparatus, the percussion member is driven by an electromagnet and retracted by a spring. This member is terminated with an active head member provided with protuberances with which the affected area is struck, causing slight lesions so that the human body is forced to act in said areas by replacing the damaged and diseased cells with other healthy ones. This percussion is accompanied with heat produced by electromagnetic waves or laser so that the atrophied tissue may soften more easily.

This percussion and heat system is affected by difficulties in adjusting the percussion intensity and there is no possibility of graduating the frequency of the impacts. Furthermore, this system uses large sized, rather unmanageable apparatus obliging the patient to adopt positions which are quite inconvenient in view of with the necessary physiological and sanitary conditions and which make focalization of the treatment to the pathological areas in question (canal routes and fossae through which vasculonerve bundles pass) harder.

OBJECTS AND SUMMARY OF THE INVENTION

It is an object of this invention to obtain stimulating regeneration of the cells with the capacitative system without the need to use an intermediate cream or slide the active electrode across the affected area.

To this end, the apparatus of the invention comprises an active metal, electrically insulated electrode, connected to a high frequency circuit and removeably coupled to a mechanical device providing it with an axial reciprocating movement. This device comprises a grip for manual application thereof to the patient's affected area, the percussion rate applied to the active electrode being adjustable. To this end, said mechanical device is connected to a box wherein there is the electronic circuit (with short-circuit protection) and the control members and elements for said rate, said box also being connected to the high frequency circuit box.

The mechanical device comprises a nozzle through which the active electrode projects. Said nozzle is provided with a removeable front end which may be replaced by a shorter or longer one, depending on whether a higher or lower percussion rate of the electrode is desired.

Said mechanical device comprises in the grip a geared motor to which a cam is connected. The rear end of an electrode holder rod bears against the periphery of the cam and the contact is assured by a spring.

This apparatus has therapeutical effects on the etiopathogenic source of the acute and chronic inflammatory process causing the pain. The stimulative cell regeneration (S.C.R.) achieved is a philosophical methodology of enzymatic and stimulative therapy of the mechanisms of the free radicals/antioxidants complex, equilibrium of the transmembrane electric potential and the phenomena of vasodilatation subsequent to the microtrauma.

BRIEF DESCRIPTION OF THE DRAWINGS

To facilitate the explanation, this description is accompanied by a sheet of drawings in which one embodiment, given only as a non-limiting example of the scope of the invention, is illustrated.

DETAILED DESCRIPTION OF THE INVENTION

Figure 1:
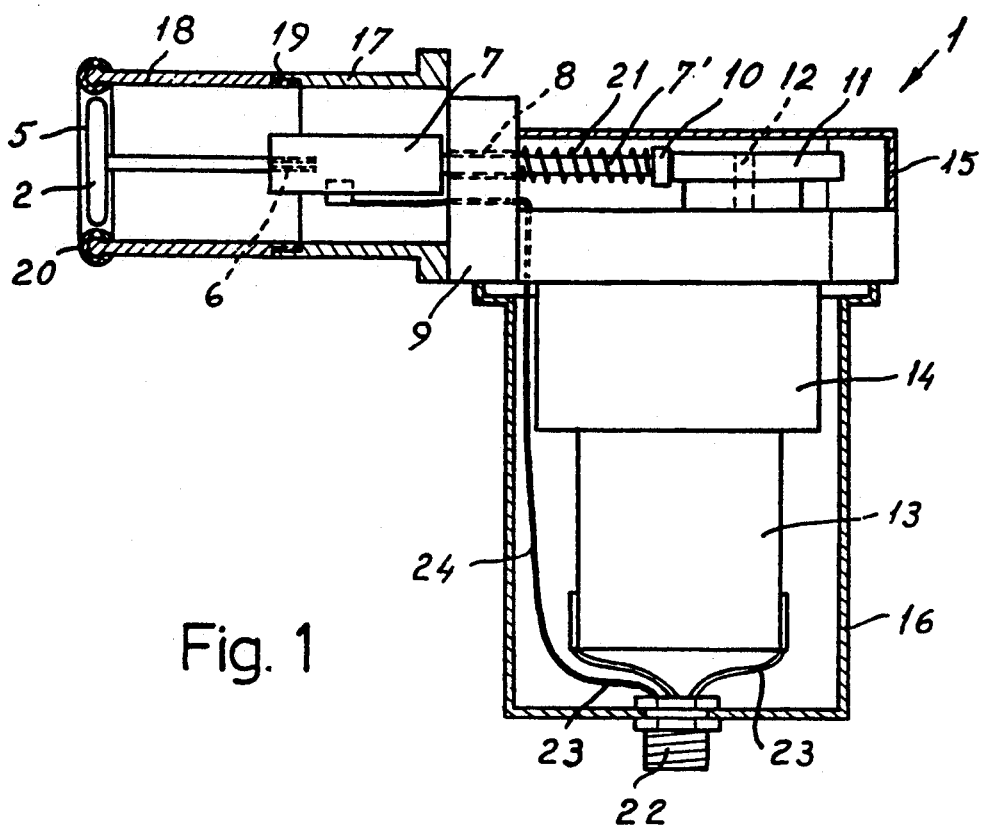
FIG. 1 is an elevation view in cross section of the mechanical device of the invention, with the electrode coupled.
Figure 2:
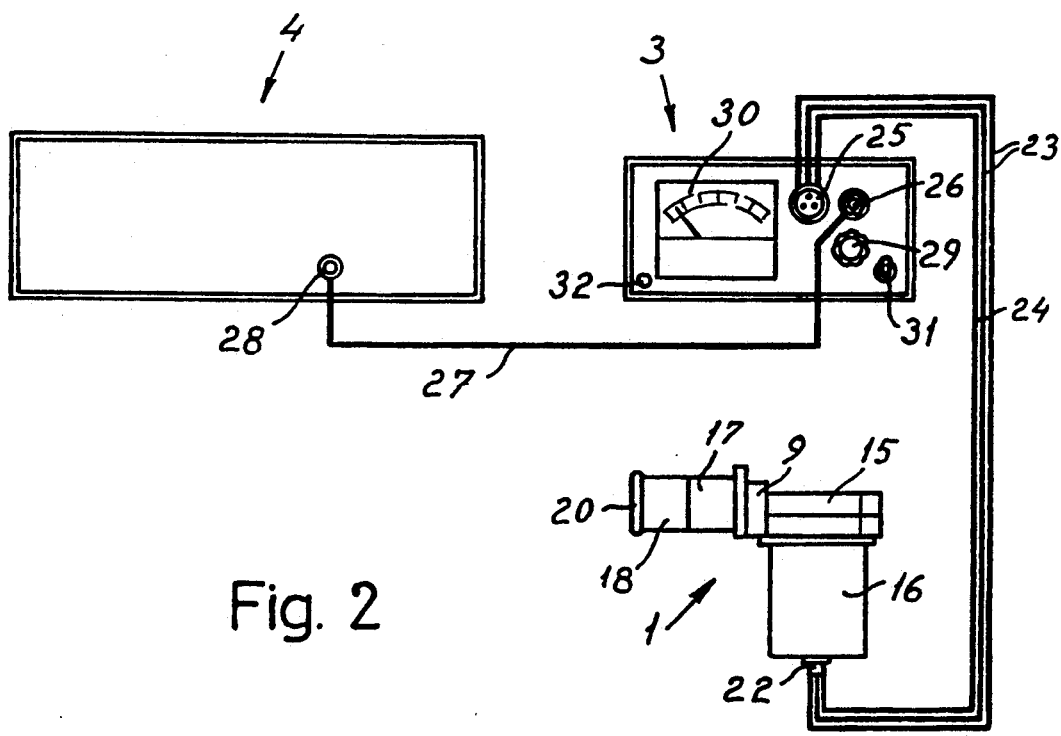
FIG. 2 is a schematic of the ensemble of parts forming this apparatus.

In accordance with the drawings, the therapeutical device comprises a mechanical device 1 driving the active electrode 2, a box 3 with the electronic circuit and the control members for the rate of axial reciprocation of the active electrode, and a box 4 in which the high frequency circuit is housed.

There will be several active electrodes 2, of varying size and shape, depending on the area of application thereof, and they will be metallic, with the active surface 5 thereof electrically isolated with a layer of appropriate material. The electrodes will be removeably screwed at an opening 6 having internal threads to a movable stem 7 guided through the passage 8 of a support 9. The rear end 10 of said stem forms a head member which bears against the periphery of a cam 11, the shaft 12 of which is driven by an electric motor 13 with reducing gear 14. This motor may be a d.c., a.c. or stepper motor.

This mechanical ensemble is housed in a box 15 which forms a grip 16 to allow for manual manipulation on the patient's affected area.

The stem 7 and the active electrode reciprocate axially in a nozzle 17 attached to the support 9 and which comprises an interchangeable front portion 18 threadedly mounted at 19 to be able to fit front portions of different length so that the electrode may project outwardly to a greater or lesser extent from the mouth of the nozzle. This mouth is terminated with a resilient ring 20 which acts as an application cushion for the device on the patient's body.

The rear head 10 of the active electrode holder stem is held engaged with the cam il by a spring 21 inserted between the support 9 and said head member and mounted around the rear portion 7' of the stem.

The base of the grip 16 is provided with a threaded connector 22 for mechanical and electrical coupling from which there, extend the supply leads 23 of the motor 13 and leads 24 for transmitting the high frequency to the electrode holder stem 7.

These leads are connected to a connector 25 of the box 3 where there is a further connector 26 for connection to the connector 28 of the box 4, where the high frequency circuit is housed, over a cable 27.

The electronic circuit of the box 3 is provided with short-circuit protection and said box is completed with the knob 29 of a potentiometer connected to the percussions per second control circuit, a voltmeter 30, a switch 31 and a warning light 32. The percussion rate will be in excess of one hundred strikes per minute and may reach up to nine hundred impacts per minute.

This adjustable impact rate is combined with the intensity of the impact which is variable and may be gentle or sharp, depending on the length of the front portion 18 of the bushing 17 surrounding the active electrode. The percussion rate and the temperature of the capacitative electrical frequency are directly proportional, and the therapeutic action is notably favered by synergy in the biological stimulation of the complex electrical-enzymatic-molecular system of the inflammatory process.

Naturally a neutral electrode for application to the patient will be connected to the box 4.

I claim:

1. An electro-mechanical apparatus for the treatment of an area of pain comprising:
    a metal active electrode having a first end and second end, said first end of said electrode being electrically insulated and being structured and arranged to be applied to an area of pain, said second end of said electrode being threaded,
    a mechanical device having a housing arranged to form a grip, said grip allowing manual manipulation of said electrode on the area of pain,
    an electrode holder stem arranged in said housing and having a first and second end, said first end of said stem contacting said second end of said electrode,
    a cam arranged in said housing and being contacted by said second end of said stem,
    spring means arranged to maintain the contact between said cam and said second end of said stem,
    drive means arranged in said housing of said mechanical device for driving said cam and thus said electrode,
    electronic circuit means having an electronic circuit housing and including a control potentiometer and connecting leads for connecting said electronic circuit means to said drive means, said electronic circuit means being coupled to said drive means to drive said electrode at a desired percussion rate of axial reciprocation, said control potentiometer having adjusting means coupled to said electronic circuit housing for adjusting the percussion rate of axial reciprocation of said electrode, and
    a high frequency circuit having a high frequency circuit housing and including a connector and a cable for connecting said high frequency circuit to said electronic circuit means, said high frequency circuit transmitting capacitively formed current of high frequency to said electrode via said electronic circuit means to provide percussion to the area of pain.

2. The apparatus of claim 1, wherein said adjusting means of said control potentiometer adjust the percussion rate of axial reciprocation of said electrode in the range of about 100 impacts per minute to about 900 impacts per minute on the area of pain.

3. The apparatus of claim 1, further comprising a nozzle in which said electrode is mounted for axial reciprocation, said first end of said electrode projecting out of said nozzle to contact the area of pain, said nozzle comprising a front portion and a rear portion, said front portion being removably coupled to said rear portion such that the intensity of the percussion of said electrode on the area of pain is controllable by interchanging front portions of different lengths.

4. The apparatus of claim 3, wherein said nozzle further comprises a resilient ring for cushioning the percussion of said electrode on the area of pain.

5. The apparatus of claim 1, further comprising a support arranged in said mechanical device, said support having a passage, said second end of said electrode holder stem being passed through said passage of said support.

6. The apparatus of claim 5, wherein said second end of said stem comprises a head member arranged to bear against said cam, said spring means being arranged between said head member and said support.

7. The apparatus of claim 1, wherein said first end of said stem has an opening having an internal thread such that said second threaded end of said electrode is engaged with said internal thread of said opening of said stem.

8. The apparatus of claim 1, wherein said drive means comprise a geared motor including an electric motor, a reducing gear, and a drive shaft, said cam being connected to said shaft.

9. The apparatus of claim 1, wherein said grip comprises a threaded connector through which said connecting leads pass.

10. The apparatus of claim 9, further comprising supply leads arranged in said housing of said mechanical device, one of said supply leads extending from said threaded connector and another one of said supply leads transmitting the high frequency current to said stem.

* * * * *

UNITED STATES PATENT AND TRADEMARK OFFICE
CERTIFICATE OF CORRECTION

PATENT NO. : 5,300,095
DATED      : April 5, 1994
INVENTOR(S) : Angel Zilvetti Salazar It is certified that error appears in the above-indentified patent and that said Letters Patent is hereby corrected as shown below:

Title page, item [19], change "Salazar" to --Zilvetti Salazar--;

item [76], change "Angel Z. Salazar" to --Angel Zilvetti Salazar--.

Signed and Sealed this

Twentieth Day of September, 1994

Attest:

BRUCE LEHMAN

*Attesting Officer*   *Commissioner of Patents and Trademarks*